United States Patent [19]
Augelli-Szafran et al.

[11] Patent Number: 5,278,326
[45] Date of Patent: Jan. 11, 1994

[54] SUBSTITUTED BETA-KETOAMIDE ACAT INHIBITORS

[75] Inventors: Corinne E. Augelli-Szafran, Ypsilanti; Bruce D. Roth, Ann Arbor, both of Mich.

[73] Assignee: Warner-Lambert Company, Morris Plains, N.J.

[21] Appl. No.: 670,667

[22] Filed: Mar. 18, 1991

[51] Int. Cl.$^5$ ............................................ C07C 233/56
[52] U.S. Cl. ...................................... 554/36; 564/74; 564/199; 568/306; 568/412
[58] Field of Search .................. 564/199, 74; 568/412, 568/306; 554/36

[56] References Cited

U.S. PATENT DOCUMENTS

| | | | |
|---|---|---|---|
| 1,989,065 | 1/1933 | Schmidt et al. | 564/199 |
| 2,432,499 | 12/1947 | Boese, Jr. | 564/199 |
| 3,600,360 | 8/1971 | Bakad | 260/78 |
| 4,014,789 | 3/1977 | Perrommet | 71/118 |
| 4,036,633 | 7/1977 | Perrommet | 71/106 |

FOREIGN PATENT DOCUMENTS 0077028  4/1983  European Pat. Off. .
84/03044  8/1984  World Int. Prop. O. .

Primary Examiner—Paul F. Shaver
Assistant Examiner—D. D. Carr
Attorney, Agent, or Firm—Michael J. Atkins

[57] ABSTRACT

Novel pharmaceutically useful compounds which lower blood cholesterol levels and are beta-ketoamides, oximes, amines, and hydroxyl derivatives thereof.

10 Claims, No Drawings

SUBSTITUTED BETA-KETOAMIDE ACAT INHIBITORS

FIELD OF INVENTION

The present invention relates to novel pharmaceutically useful compounds, compositions containing said compounds, and a method of using said compounds to lower blood cholesterol levels.

BACKGROUND OF THE INVENTION

This invention relates to chemical compounds having pharmacological activity, to pharmaceutical compositions which include these compounds, and to a pharmaceutical method of treatment. More particularly, this invention concerns certain novel compounds which inhibit the enzyme acylcoenzyme A: cholesterol acyltransferase (ACAT), pharmaceutical compositions containing these compounds, and a method of treating hypercholesterolemia and atherosclerosis.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which could be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

INFORMATION DISCLOSURE STATEMENT

Compounds of the following formula are disclosed as intermediates to prepare crotonanilide herbicides in U.S. Pat. No. 4,014,679, issued Mar. 29, 1977:

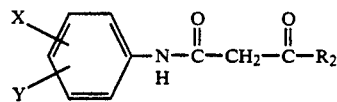

wherein $R_2$ is alkyl $C_{1-6}$, and X and Y are hydrogen, halogen, lower alkyl $C_{1-6}$ optionally substituted with at least one halogen, alkoxy of 1 to 3 carbon atoms, alkylthio and alkylsulfinyl of 1 to 6 carbon atoms, acyl of an organic carboxylic acid of 1 to 6 carbon atoms, $NO_2$ and $CF_3$.

U.S. Pat. No. 4,036,633, issued Jul. 19, 1977 describes compounds of the following general formula as intermediates in the preparation of pre- and post-emergence crotonanilides:

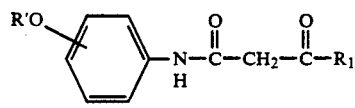

wherein R' is hydrogen or

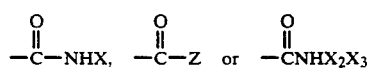

wherein X is alkyl $C_{1-8}$ alkoxyalkyl $C_{2-12}$, or cycloalkyl $C_{3-7}$, Z is alkyl $C_{1-6}$, $X_2$ is alkyl $C_{1-3}$ and X is alkyl $C_{1-3}$ or alkoxy $C_{1-3}$; and $R_1$ is alkyl $C_{1-3}$.

U.S. Pat. No. 3,600,360 describes the following compound as intermediate in the manufacture of polyamides:

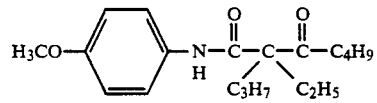

SUMMARY OF THE INVENTION

Compounds of the following general Formula I are useful in lowering blood cholesterol:

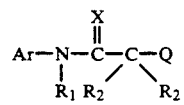

Formula I wherein Y is oxygen or sulfur;
wherein Ar is
(a) phenyl which is unsubstituted or is substituted with from 1 to 3 substituents selected from
  alkyl having from 1 to 6 carbon atoms and which is straight or branched,
  alkoxy having from 1 to 6 carbon atoms and which is straight or branched;
  phenoxy,
  hydroxy,
  fluorine,
  chlorine,
  bromine,
  nitro,
  trifluoromethyl,
  —COOH, —COOalkyl wherein alkyl has from 1 to 4 carbon atoms, —NR$_4$R$_5$ wherein R$_4$ and R$_5$ are independently hydrogen or alkyl of from 1 to 4 carbon atoms;

wherein R$_1$ is hydrogen or a lower alkyl group having from 1 to 4 carbon atoms;

wherein each R$_2$ is hydrogen, a lower alkyl group having from 1 to 4 carbon atoms or each R$_2$ taken together with the carbon atom to which it is attached forms a carbocyclic ring of from 3 to 6 carbon atoms;

wherein Q is

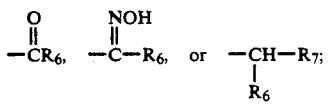

wherein R$_6$ is (a) phenyl which is unsubstituted or is substituted with from 1 to 3 substituents selected from alkyl having from 1 to 6 carbon atoms and which is straight or branched, alkoxy having from 1 to 6 carbon atoms and which is straight or branched, phenoxy, hydroxy, fluorine, chlorine, bromine, nitro, trifluoromethyl,

—COOH,

—COOalkyl wherein alkyl has from 1 to 4 carbon atoms,

—NR$_4$R$_5$ wherein R$_4$ and R$_5$ are as defined above;

(b) the group

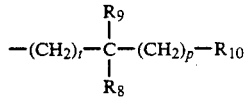

wherein t is zero to 4; p is zero to 4 with the proviso that the sum of t and p is not greater than 5; R$_8$ and R$_9$ are independently selected from hydrogen or straight or branched alkyl having from 1 to 6 carbon atoms, or when R$_8$ is hydrogen, R$_9$ can be selected from the groups defined for R$_{10}$; and R$_{10}$ is phenyl or phenyl substituted with from 1 to 3 substituents selected from straight or branched alkyl having from 1 to 6 carbon atoms, straight or branched alkoxy having from 1 to 6 carbon atoms, straight or branched thioalkoxy having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or NR$_4$R$_5$ wherein R$_4$ and R$_5$ having the meanings defined above;

(c) a straight or branched hydrocarbon chain having from 1 to 20 carbon atoms and which is saturated or contains from 1 to 3 double bonds;

(d) the group

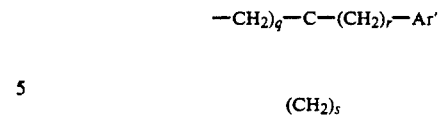

wherein q is zero or one to three; r is zero, one or two; s is two to six; and Ar' is phenyl or phenyl substituted with from 1 to 3 substituents selected from alkyl of from 1 to 6 carbon atoms and which is straight or branched, alkoxy of from 1 to 6 carbon atoms and which is straight or branched, hydroxy, benzyloxy, fluorine, chlorine, bromine, nitro, trifluoromethyl,

—NH—COCH$_3$,

—CONH$_2$,

—COOH,

—COOalkyl wherein alkyl has from 1 to 4 carbon atoms and which is straight or branched,

—CH$_2$COOH,

—CH$_2$CONH$_2$,

—(CH$_2$)$_v$NR$_4$R$_5$ wherein v is one or two and R$_4$ and R$_5$ have the meanings defined above;

(e) anthracene;

(f) —(CH$_2$)$_n$—OR wherein R is hydrogen or 2-tetrahydropyran, and n is a number of from 5 to 16;

(g) 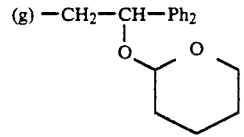

or, (h) the group 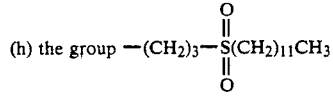

wherein R$_7$ is hydroxy or NH$_2$; and pharmaceutically acceptable salt thereof.

DETAILED DESCRIPTION OF THE INVENTION

The present invention provides a novel class of compounds which are substituted β-ketoamides and derivatives thereof and which are ACAT inhibitors rendering them useful in treating hypercholesterolemia and atherosclerosis.

In the compounds of Formula I illustrative examples of straight or branched saturated hydrocarbon chains having from 1 to 20 carbon atoms include methyl, ethyl, n-propyl, isopropyl, n-butyl, isobutyl, tert-butyl, n-pentyl, isopentyl, n-hexyl, n-heptyl, n-octyl, n-undecyl, n-dodecyl, n-hexadecyl, 2,2-dimethyldodecyl, 2-ethyltetradecyl, and n-octadecyl groups.

Illustrative examples of straight or branched hydrocarbon chains having from 1 to 20 carbon atoms and having from 1 to 3 double bonds include ethenyl, 2- propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having from 1 to 6 carbon atoms include, for example, methoxy, ethoxy, n-propoxy, t-butoxy, and pentyloxy.

Illustrative of straight or branched thioalkoxy groups having from 1 to 6 carbon atoms are methylthio, ethylthio, n-propylthio, isopropylthio, and butylthio. The thioalkoxy group may also be referred to as alkylthio.

Illustrative examples of straight or branched alkyl groups having from 1 to 4 or 1 to 6 carbon atoms include methyl, ethyl n-propyl, isopropyl n-butyl, tert-butyl, pentyl, and hexyl.

In the groups Ar and Ar' which may be substituted phenyl, the substituents vary in number from 1 to 3, may be the same or different and may be attached to any available position on the aromatic ring.

The compounds of general Formula I are substituted $\beta$-ketoamides as depicted by the following general Formula II, oximes thereof as depicted by the following general Formula III or other derivative thereof as depicted by the following general Formula IV.

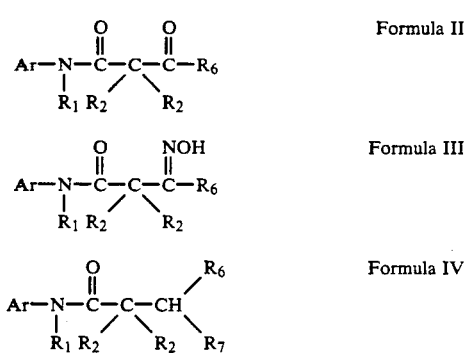

In the above general Formulas II, III, and IV the various substituents Ar, $R_1$, $R_2$, $R_6$, and $R_7$ have the meanings defined in general Formula I.

Pharmaceutically acceptable salts of the compounds of Formula I are also included as a part of the present invention.

The base salts may be generated from compounds of Formula I by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Stephen N. Berge, et al, J Pharm Sci 16, 1-19 (1977).

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

Certain compounds of the present invention may also exist in different stereoisomeric forms by virtue of the presence of asymmetric centers in the compound. The present invention contemplates all stereoisomeric forms of the compounds as well as mixtures thereof, including racemic mixtures. Individual stereoisomers may be obtained, if desired, by methods known in the art as, for example, the separation of stereoisomers on chiral chromatographic columns.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

Preferred compounds of this invention are those wherein Q represents

More preferred compounds are those wherein $R_6$ represents groups (a), (b), and (c) defined above. Also preferred are compounds wherein Ar represents phenyl substituted with alkyl substitution in the 2- and 6-positions being more preferred.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in F. J. Field and R. G. Salone, Biochemica et Biophysica 712:557-570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table 1 where they are expressed as $IC_{50}$ values; i.e., the concentration of test compound required to inhibit the activity of the enzyme by 50%.

TABLE 1

| Compound of Example | $IC_{50}$ ($\mu$M) |
| --- | --- |
| 1 | 0.81 |
| 2 | 0.035 |
| 3 | 0.044 |
| 4 | 0.011 |
| 5 | 0.069 |
| 6 | 0.057 |
| 7 | 0.23 |
| 8 | 0.15 |
| 9 | 1.0 |
| 10 | >1 |
| 11 | 0.374 |
| 12 | >1 |

TABLE 1-continued

| Compound of Example | $IC_{50}$ ($\mu M$) |
| --- | --- |
| 13 | >1 |
| 14 | 0.011 |
| 15 | 0.006 |
| 16 | 0.097 |
| 17 | 0.060 |
| 18 | 0.024 |
| 21 | 0.210 |
| 22 | 3.492 |

Another test used to evaluate the compounds of the present invention is an in vivo screen designated APCC. In this test male Sprague-Dawley rats (200 to 225 g) are randomly divided into treatment groups and dosed at 4 PM with either vehicle (CMC/Tween) or suspensions of compounds in vehicle. The normal chow diet is then replaced with the PCC diet with either 1% or 0.5% cholic acid, as indicated. The rats consume this diet ad libitum during the night and are sacrificed at 8 AM to obtain blood samples for cholesterol analysis using standard procedures. Statistical differences between mean cholesterol values for the same vehicle are determined using analysis of variance followed by Fisher's least significant test.

In therapeutic use as agents for treating hypercholesterolemia or atherosclerosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid,. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner cachets are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

Compounds of Formula I wherein Q is

and $R_1$ and $R_2$ are hydrogen are prepared as set forth in Chart I hereof.

The $\beta$-ketoester intermediate (B) was obtained by first reacting carboxylic acid (A) with 1,1'-carbonyldiimidazole followed by the magnesium salt of ethyl potassium malonate in the presence of triethylamine. Treatment of ester (B) with 1,4-diazabicyclo[2.2.2]octane yielded methyl ketone (C). Formation of the lithioenolate of intermediate (C) followed by the addition of the desired aryl isocyanate or thioisocyanate yielded the desired $\beta$-ketoamides (D). The compounds of formula (D) can be further treated with an appropriate alkyl halide in the presence of base by procedures well known in the art to give compounds of Formula I wherein $R_1$ and $R_2$ are other than hydrogen.

The compounds of Formula I wherein Q is

and $R_1$ may be hydrogen, and $R_2$ is other than hydrogen can be prepared as set forth in Chart II hereof.

Treatment of the ethyl ester (E) with LDA followed by the addition of an appropriate acid chloride yields the $\beta$-keto ethyl ester intermediate (F). Treatment of (F) with trimethylaluminum followed by an appropriate aniline group yields the desired $\beta$-ketoamide (G). The compounds of formula (G) could be treated with an alkyl halide in the presence of base to give compounds of Formula I wherein $R_1$ is other than hydrogen.

The compounds of Formula I wherein Q is

are prepared from the corresponding compounds wherein Q is

by treatment with hydroxylamine hydrochloride in the presence of sodium acetate. The oximes can be converted to compounds of Formula I wherein Q is

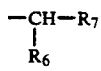

and $R_7$ is $NH_2$ by treatment with Raney nickel in the presence of methanol and ammonia. Compounds of Formula I wherein $R_7$ is OH are prepared by treating the corresponding compound wherein Q is

with sodium borohydride.

EXAMPLE 1

Preparation of N-[2,6-bis(1-methylethyl)phenyl]-β-oxo-benzene-propanamide

To a cooled ($-78°$ C.) solution of diisopropylamine (2.48 g, 0.024 mol) in 100 mL ether, n-BuLi (0.024 mol) was added dropwise followed by 50 mL ether. After stirring for 5 minutes at $-78°$ C. under a nitrogen atmosphere, a solution of acetophenone (2.95 g, 0.024 mol) in 25 mL ether was added dropwise and the resulting solution was stirred for 20 minutes at $-78°$ C. A solution of 2,6-diisopropylphenyl isocyanate in 25 ML $Et_2O$ was then added dropwise and the reaction mixture was allowed to gradually warm to room temperature and stir for 16 hours under a nitrogen atmosphere (J. F. Wolfe, et al, Synthetic Communications 17, 13 (1987)). The reaction mixture was then quenched with a saturated solution of ammonium chloride and extracted with methylene chloride. The layers were separated and the organic layer was washed two times with water, dried ($Na_2SO_4$) and concentrated in vacuo (30° C.) to afford a yellow residue. This residue was washed with hexane, filtered, and oven-dried (40° C.) to yield a pale yellow solid, 4.3 g (0.013 mol, 54%) of the title compound, mp 124°-126° C.

Analysis for $C_{21}H_{25}NO_2$: Calcd: C, 77.99; H, 7.79; N, 4.33; Found: C, 77.72; H, 7.90; N, 4.17.

EXAMPLE 2

Preparation of N-[2,6-bis(1-methylethyl)phenyl]-β-oxo-γ-phenyl-benzenebutanamide The title compound, mp 153°-155° C., was prepared from 1,1-diphenylacetone (5.0 g, 0.023 mol), 2,6-diisopropylphenyl isocyanate (4.6 g, 0.023 mol) and lithium diisopropylamide (0.023 mol) using the procedure described in Example 1.

Analysis for $C_{28}H_{31}NO_2$: Calcd: C, 81.31; H, 7.55; N, 3.38; Found: C, 80.75; H, 7.84; N, 3.01.

EXAMPLE 3

Preparation of N-[2,6-bis(1-methylethyl)phenyl]-β-oxo-δ-phenyl-benzenepentanamide Step A: Preparation of β-oxo-δ-phenyl-benzene pentanoic acid ethyl ester To a cooled solution (0° C.) of 3,3-diphenylpropionic acid (50.0 g, 0.220 mol) in 300 mL THF, 1,1'-carbonyldiimidazole (43.0 g, 0.265 mol) was added portionwise (exotherm to 10° C.) and stirred at 0° C. for 3 hours. After 3 hours, in a separate flask (equipped with an overhead stirrer), magnesium chloride (40.0 g, 0.418 mol) was added to a cooled solution (0° C.) of ethyl potassium malonate (60.0 g, 0.352 mol) in 400 mL acetonitrile (exotherm to 30° C.). Triethylamine (48.9 g, 0.484 mol) was then added and this mixture and the 3,3-diphenylpropionic acid mixture were separately allowed to gradually warm to room temperature and stir for 4 hours. The propionic acid mixture was then added dropwise to the malonate mixture (exotherm to 30° C.) and this reaction mixture was stirred at room temperature for 16 hours. This pale yellow heterogeneous reaction mixture was then carefully quenched with a solution of 200 g sodium bisulfate in 700 mL water. Ethyl acetate (3L) was then added to the yellow homogeneous solution, the layers were separated, and the organic layer was washed with 1L 5% NaOH solution and 1L saturated NaCl solution. The organic layer was then diluted with 1.5L hexane, dried ($MgSO_4$), and concentrated in vacuo (30° C.) to give a yellow oil. Purification by flash chromatography (silica gel, 15% EtOAc/hexane) yielded 33.2 g (0.112 mol, 51%) of the desired product.

Analysis for $C_{19}H_{20}O_3$: Calcd: C, 77.00; H, 6.80; Found: C, 77.10; H, 6.77.

Step B: Preparation of 4,4-diphenylbutan-2-one

To a solution of β-oxo-δ-phenyl-benzene pentanoic acid ethyl ester (8.0 g, 0.026 mol) in 47.5 mL xylenes (15.0 eq), 1,4-diazabicyclo[2.2.2]octane (30.28 g, 0.269 mol, 10 eq) was added and the reaction mixture was first heated to reflux for 5 hours and then stirred at room temperature for 16 hours (D. H. Miles, et al, J. Org. Chem. 39, 2647 (1974)). The reaction mixture was then acidified (pH 1) with approximately 10 mL 5% HCl. This heterogeneous mixture was then filtered through Celite, thoroughly washing the bed of Celite with ether. The organic layer was washed with water, dried ($MgSO_4$), and concentrated in vacuo to give a crude oil. Purification by flash chromatography (silica gel, 15% EtOAc/hexane) yielded 4.0 g (0.018 mol, 70%) of the desired product.

Analysis for $C_{16}H_{16}O$: Calcd: C, 85.67; H, 7.19; Found: C, 85.96; H, 7.58.

Step C: Preparation of N-(2,6-bis(1-methylethyl)phenyl]-β-oxo-δ-phenyl-benzene-pentanamide The title compound, mp 146°-148° C., was prepared from 4,4-diphenylbutan-2-one (3.50 g, 0.015 mol), 2,6-diisopropylphenyl isocyanate (3.17 g, 0.015 mol) and lithium diisopropylamide (0.015 mol) using the procedure described in Example 1.

Analysis for $C_{29}H_{33}NO_2$: Calcd: C, 81.46; H, 7.77; N, 3.27; Found: C, 81.62; H, 7.89; N, 3.14.

EXAMPLE 4

Preparation of
N-[2,6-bis(1-methylethyl)phenyl]-β-oxo-1-phenyl-cyclopentanepropanamide

Step A: Preparation of
β-oxo-1-phenylcyclopentanepropanoic acid ethyl ester

The title compound was prepared from 1-phenyl-1-cyclopentanecarboxylic acid (50.0 g, 0.220 mol), 1,1'-carbonyldiimidazole (43.0 g, 0.265 mol), magnesium chloride (40.0 g, 0.418 mol), ethyl potassium malonate (60.0 g, 0.352 mol), and triethylamine (48.9 g, 0.484 mol) using the procedure described in Example 3, Step A.

Analysis for $C_{16}H_{20}O_3$: Calcd: C, 73.81; H, 7.74; Found: C, 74.04; H, 7.46.

Step B: Preparation of 1-phenyl, 1-cyclopentylacetone

The title compound was prepared from β-oxo-1-phenylcyclopentanepropanoic acid ethyl ester (8.0 g, 0.03 mol), 1,4-diazabicyclo[2.2.2]octane (34.4 g, 0.30 mol) and xylenes (54.8 ML, 15.0 eq) using the procedure described in Example 3, Step B. $^1H$ NMR (ppm, $CDCl_3$): 1.62–1.73 (m, 4H), 1.85–1.90 (m, 2H), 1.93 (s, 3H, $CH_3$), 2.43–2.52 (m, 2H), 7.20–7.36 (m, 5H).

Step C: Preparation of
N-[2,6-bis(1-methylethyl)phenyl]-β-oxo-1-phenyl-cyclopentanepropanamide The title compound, mp 145°–147° C., was prepared from 1-phenyl, 1-cyclopentylacetone (21.0 g, 0.011 mol), 2,6-diisopropylphenyl isocyanate (2.23 g, 0.011 mol) and lithium diisopropylamide (0.011 mol) using the procedure described in Example 1.

Analysis for $C_{26}H_{33}NO_2$: Calcd: C, 79.77; H, 8.49; Found: C, 79.91; H, 8.64.

EXAMPLE 5

Preparation of
N-[2,6-bis(1-methylethyl)phenyl]-3-oxo-tetradecanamide

The title compound was prepared from 2-tridecanone (10.0 g, 0.050 mol), 2,6-diisopropylphenyl isocyanate (10.16 g, 0.050 mol) and lithium diisopropylamide (0.050 mol) using the procedure described in Example 1. Purification by flash chromatography (silica gel, 15% EtOAc/hexane) yielded 13.14 g (0.032 mol, 65%) of the desired product.

Analysis for $C_{26}H_{43}NO_2$: Calcd: C, 77.75; H, 10.79; N, 3.48; Found: C, 77.55; H, 11.26; N, 3.37.

EXAMPLE 6

Preparation of
N-[2,6-bis(1-methylethyl)phenyl]-3-oxo-14-[(tetrahydro-2H-pyran-2-yl)oxyltetradecanamide

Step A: Preparation of
12-[(tetrahydro-2H-pyran-2-yl)oxy]-dodecanoic acid

To a solution of 12-hydroxydodecanoic acid (10.0 g, 0.046 mol) in 150 mL THF, p-toluenesulfonic acid (0.087 g, 0.01 eq) was added followed by 3,4-dihydro-2H-pyran (5.95 g, 0.070 mol). After stirring this homogeneous reaction mixture for 16 hours at room temperature under a nitrogen atmosphere, $NaHCO_3$ saturated solution was added to the mixture. The mixture was then extracted with methylene chloride, dried ($MgSO_4$), and concentrated in vacuo (30° C.) to yield 13.0 g (0.043 mol, 94%) of the desired product.

Analysis for $C_{17}H_{32}O_4$: Calcd: C, 67.95; H, 10.73; Found: C, 67.72; H, 10.70.

Step B: Preparation of
3-oxo-14-[(tetrahydro-2H-pyran-2-yl)oxy]-tetradecanoic acid ethyl ester The title compound was prepared from 12-[(tetrahydro-2H-pyran-2-yl)oxy]-dodecanoic acid (10.0 g, 0.033 mol), 1,11-carbonyldiimidazole (6.47 g, 0.039 mol), magnesium chloride (6.02 g, 0.063 mol), ethyl potassium malonate (9.06 g, 0.053 mol), and triethylamine (7.40 g, 0.073 mol) using the procedure described in Example 3, Step A.

$^1H$ NMR (ppm, $CDCl_3$): 1.26–1.82 (m, 20H), 2.50–2.55 (t, 3H, $CH_2CH_3$, J=8.79 Hz), 3.33–3.87 (m, 8H), 3.43 (s, $COCH_2CO$), 4.15–4.24 (q, 2H, $CH_2CH_3$, J=8.57 Hz), 4.57 (m, 1H).

Step C: Preparation of
13-[(tetrahydro-2H-pyran-2-yl)oxy]-2-tridecanone

The title compound was prepared from 3-oxo-14-[(tetrahydro-2H-pyran-2-yl)oxy]-tetradecanoic acid ethyl ester (7.97 g, 0.021 mol), 1,4-diazabicyclo-[2.2.2]octane (24.13 g, 0.215 mol), and xylenes (39.3 mL, 15 eq) using the procedure described in Example 3, Step B.

MS: 299.3 (MH+), 298.3 (M+).

Step D: Preparation of
N-[2,6-bis(1-methylethyl)phenyl]-3-oxo-14-[(tetrahydro-2H-pyran-2-yl)oxy]-tetradecanamide The title compound was prepared from 13-[(tetrahydro-2H-pyran-2-yl)oxy]-2-tridecanone (2.0 g, 0.006 mol), 2,6-diisopropylphenyl isocyanate (1.36 g, 0.006 mol), and lithium diisopropylamide (0.006 mol) using the procedure described in Example 1. Purification by flash chromatography (silica gel, 10% EtOAc/hexane) yielded 3.11 g (0.006 mol, 93%) of the desired product.

MS: 502.4 (MH+), 501.4 (M+).

EXAMPLE 7

Preparation of
N-[2,6-bis(1-methylethyl)phenyl]-14-hydroxy-3-oxo-tetradecanamide To a solution of N-[2,6-bis(1-methylethyl)phenyl]-3-oxo-14-[(tetrahydro-2H-pyran-2-yl)oxyltetradecanamide (0.97 g, 0.001 mol; see Example 6 for preparation) in 190 mL 95% MEOH, p-toluenesulfonic acid (0.055 g, 0.15 eq) was added and the reaction mixture was stirred for 16 hours at room temperature under a nitrogen atmosphere. The reaction mixture was then concentrated in vacuo (30° C.) to give a tacky residue. This residue was diluted with water and chloroform, the layers were separated and the aqueous layer was then extracted three times with chloroform. The combined organic layers were then washed two times with saturated NaCl solution, dried ($MgSO_4$), and concentrated in vacuo to yield 0.63 g (0.001 mol, 79.4%) of the desired product.

MS: 418.4 (MH+), 417.4 (M+).

EXAMPLE 8

Preparation of
3-oxo-N-(2,4,6-trimethoxyphenyl)tetradecanamide

Step A: Preparation of
2,4,6-trimethoxyphenylisocyanate

To a heated solution (70° C.) of phosgene in toluene (12.5% solution, 230 ML, 2.5 eq), 2,4,6-trimethoxyaniline (25.0 g, 0.113 mol) was added portionwise. The reaction mixture was heated to reflux for 4 hours and then stirred at room temperature for 16 hours. The reaction mixture then concentrated in vacuo. The residue was rinsed two times with ether and concentrated in vacuo. Ether was again added to the residue and cooled in an ice bath for 2 hours. The solid was filtered, rinsed with ether, and oven-dried to yield the desired product.

Analysis for $C_{16}H_{11}NO_4$: Calcd: C, 57.41; H, 5.30; N, 6.69; Found: C, 57.41; H, 5.26; N, 6.45.

Step B: Preparation of
3-oxo-N-(2,4,6-trimethoxyphenyl)-tetradecamide

The title compound, mp 95°–98° C., was prepared from 2-tridecanone (3.57 g, 0.018 mol), 2,4,6-trimethoxyphenylisocyanate (3.80 g, 0.018 mol), and lithium diisopropylamide (0.018 mol) using the procedure described for Example 1.

EXAMPLE 9

Preparation of
N,2,2-trimethyl-3-oxo-N-[2,6-bis(1-methylethyl)-phenyl]-tetradecanamide To a cooled solution (0° C.) of NaH (0.018 mol, 2.0 eq) in 25 mL THF, N-[2,6-bis(1-methylethyl)phenyl]-3-oxo-tetradecanamide (4.0 g, 0.009 mol, see Example 5 for preparation) in 10 mL THF was added dropwise (exotherm from 0° C.-5° C.). The resulting reaction mixture was then stirred for 30 minutes at 0° C. under a nitrogen atmosphere. Iodomethane (2.55 g, 0.018 mol) was then added dropwise and the reaction mixture was then allowed to gradually warm to room temperature and stir for 16 hours. The mixture was then quenched with H$_2$O and extracted with ether. The layers were separated and the organic layer was then washed with brine, dried (MgSO$_4$), and concentrated in vacuo (30° C.) to yield 2.66 g (0.006 mol, 66.6%) of the desired product.

MS: 444.0 (MH+), 443.0 (M+).

EXAMPLE 10

Preparation of
N,2,2-trimethyl-3-oxo-N-(2,4,6-trimethoxyphenyl)-tetradecanamide

The title compound was prepared from 3-oxo-N-(2,4,6-trimethoxyphenyl)-tetradecanamide (1.23 g, 0.003 mol), sodium hydride (0.290 g, 0.006 mol), and iodomethane (0.850 g, 0.006 mol) using the procedure described in Example 11. Purification by flash chromatography (silica gel, 50% EtOAc/hexane) yielded 0.460 g (0.001 mol, 34%) of the desired compound.

MS: 450.3 (MH+), 449.3 (M+).

EXAMPLE 11

Preparation of
2,2-dimethyl-3-oxo-N-(2,4,6-trimethoxyphenyl)-tetradecanamide

Step A: Preparation of
2,2-dimethyl-3-oxo-tetradecanoic acid ethyl ester

To a cooled solution (−78° C.) of diisopropylamine (2.22 g, 0.022 mol) in 25 mL ether, n-BuLi (0.022 mol) was added dropwise and stirred for 20 minutes under a nitrogen atmosphere. Ethyl isobutyrate (2.65 g, 0.022 mol) was then added dropwise and the mixture was stirred for 20 minutes. In a separate flask, lauroyl chloride (5.0 g, 0.022 mol) was stirred in 10 mL ether and cooled to 0° C. The ethyl isobutyrate enolate solution was added dropwise to the lauroyl chloride solution over a 5-minute period. The reaction mixture was allowed to gradually warm to room temperature and stir for 16 hours (M. W. Rathke, et al, Tet. Lett., 2953 (1971)). The mixture was quenched with saturated ammonium chloride solution and extracted with ether two times. The combined organic layers were washed with brine, dried (MgSO$_4$), and concentrated in vacuo (30° C.) to yield 6.5 g (0.021 mol, 98.9%) of the title compound.

MS 299.2 (MH+), 298.2 (M+).

Step B: Preparation of
2,2-dimethyl-3-oxo-N-(2,4,6-trimethoxyphenyl)-tetradecanamide To a flask containing 10 mL benzene which had been flushed with nitrogen, trimethylaluminum (2.0M hexane solution, 0.003 mol, 1.14 eq) was added dropwise and cooled to 5° C. A solution of 2,4,6-trimethoxyaniline (0.653 g, 0.003 mol) in 1.5 mL benzene was added dropwise (exotherm to 10° C.) and stirred for 20 minutes at 5° C. The ice bath was removed and the contents were allowed to gradually warm to room temperature over a 45-minute period. A solution of 2,2-dimethyl-3-oxo-tetradecanoic acid ethyl ester (1.0 g, 0.003 mol) in 1.5 mL benzene was added dropwise and the resulting reaction mixture was heated to reflux for 16 hours (M. F. Lipton, et al, Org. Syn. Coll. Vol. 2, 492). After cooling to room temperature, the mixture was hydrolyzed slowly with 2% HCl solution (5 mi) and stirred for 20 minutes. The layers were then separated and the aqueous layer was extracted three times with ethyl acetate. The combined organic layers were washed with brine, dried (MgSO$_4$), and concentrated in vacuo (30° C.) to yield a residue which was washed with hot hexanes, cooled, filtered, and oven-dried to yield 0.340 g (0.78 mmol, 26%) of the title compound, mp 92°–94° C.

MS 463.3 (MH+), 435.3 (M+).

EXAMPLE 12

Preparation of
2,4-difluoro-N-octyl-β-oxo-benzenepropanamide

The title compound was prepared from 2',4'-difluoroacetophenone (5.0 g, 0.032 mol), octyl isocyanate (4.97 g, 0.032 mol), and lithium diisopropylamide (0.032 mol) using the procedure described in Example 1. Purification by flash chromatography (silica gel, 20% EtOAc/hexane) yielded 4.25 g (0.013 mol, 42.6%) of the desired product.

MS: 312.22 (MH+), 311.22 (M+).

EXAMPLE 13

Preparation of N-octyl-β-oxo-9-anthracenepropanamide

The title compound, mp 70°-72° C., was prepared from 9-acetylanthracene (5.0 g, 0.022 mol), octyl isocyanate (3.52 g, 0.022 mol), and lithium diisopropylamide (0.032 mol) using the procedure described in Example 1. Purification by flash chromatography (silica gel, 5% EtOAc/hexane) yielded 3.84 g (0.010 mol, 45.2%) of the desired product.

Analysis for $C_{25}H_{29}NO_2$: Calcd: C, 79.96; H, 7.78; N, 3.73; Found: C, 80.07; H, 7.94; N, 3.62.

EXAMPLE 14

Preparation of N-[2,6-bis(1-methylethyl)phenyl]-3-oxo-pentadecanamide

The title compound was prepared from 2-tetradecanone (5.0 g, 0.023 mol), 2,6-diisopropylphenylisocyanate (4.78 g, 0.023 mol), and lithium diisopropylamide (0.023 mol) using the procedure described in Example 1. Purification by flash chromatography (silica gel, 15% EtOAc/hexane) yielded 4.25 g (0.010 mol, 44%) of the desired product.

Analysis for $C_{27}H_{45}NO_2$: Calcd: C, 78.02; H, 10.91; N, 3.37; Found: C, 77.76; H, 10.76; N, 3.67.

EXAMPLE 15

Preparation of N-[2,6-bis(1-methylethyl)phenyl]-3-oxo-hexadecanamide

The title compound was prepared from 2-pentadecanone (3.0 g, 0.013 mol), 2,6-diisopropylphenyl isocyanate (2.64 g, 0.013 mol), and lithium diisopropylamide (0.013 mol) using the procedure described in Example 1. Purification by flash chromatography (silica gel, 15% EtOAc/hexane) yielded 1.92 g (0.004, 34%) of the desired product.

MS: 430 (MH+), 429 (M+).

EXAMPLE 16

Preparation of N-[2,6-bis(1-methylethyl)phenyl]-3-oxo-dodecanamide

The title compound was prepared from 2-undecanone (5.0 g, 0.029 mol), 2,6-diisopropylphenyl isocyanate (5.96 g, 0.029 mol), and lithium diisopropylamide (0.029 mol) using the procedure described in Example 1. The desired product was obtained in 79.4% yield (8.6 g, 0.023 mol).

Analysis for $C_{24}H_{39}NO_2$: Calcd: C, 77.16; H, 10.52; N, 3.75; Found: C, 76.99; H, 10.74; N, 3.96.

EXAMPLE 17

Preparation of N-r2,6-bis(1-methylethyl)phenyl]-3-oxo-tridecanamide

The title compound was prepared from 2-dodecanone (5.0 g, 0.027 mol), 2,6-diisopropylphenyl isocyanate (5.51 g, 0.027 mol), and lithium diisopropylamide (0.027 mol) using the procedure described in Example 1. The desired product was obtained in 85.6% yield (9.0 g, 0.023 mol).

Analysis for $C_{25}H_{41}NO_2$: Calcd: C, 77.47; H, 10.66; N, 3.61; Found: C, 77.11; H, 10.96; N, 3.86.

EXAMPLE 18

Preparation of N-[2,6-bis(1-methylethyl)phenyl]-3-oxo-heptadecanamide

The title compound was prepared from 2-hexadecanone (5.0 g, 0.018 ml), 2,6-diisopropylphenyl isocyanate (3.72 g, 0.018 mol), and lithium diisopropylamide (0.018 mol) using the procedure described in Example 1. The desired product was obtained in 80% yield (6.38 g, 0.014 mol). MS: 443 (M+).

EXAMPLE 19

Preparation of N-[2,6-bis(1-methylethylphenyl]-β-oxo-δ-phenyl-δ-[(tetrahydro-2H-pyran-2-yl)oxy]benzenepentanamide

Step A: Preparation of β-oxo-δ-phenyl-δ-(tetrahydro-2H-pyran-2-yl)oxybenzenepentanoic acid ethyl ester The title compound (J. W. Wolfe, et al, J. Org. Chem. 29, 3249 (1964) ) was prepared from δ-hydroxy-β-oxo-δ-phenylbenzenepentanoic acid ethyl ester (2.0 g, 0.006 mol), p-toluenesulfonic acid (0.014 g, 0.60 mmol), and 3,4-dihydro-2H-pyran (0.77 g, 0.009 mol) using the procedure described in Example 6, Step A.

MS: 295 (MH+).

Step B: Preparation of 4-phenyl-4-(tetrahydro-2H-pyran-2-yl)oxy-benzenebutan-2-one The title compound was prepared from β-oxo-δ-phenyl-δ-(tetrahydro-2H-pyran-2-yl)oxy-benzene pentanoic acid ethyl ester (2.28 g, 0.005 mol) 1,4-diazabicyclo[2.2.2]octane (6.45 g 0.057 mol), and xylenes (10.5 mL, 15.0 eq) using the procedure described in Example 3, Step B.

Step C: Preparation of N-[2,6-bis(1-methylethyl)phenyl]-β-oxo-δ-phenyl-δ-[(tetrahydro-2H-pyran-2-yl)oxy]benzenepentanamide The title compound was prepared from 4-phenyl-4-(tetrahydro-2H-pyran-2-yl)oxy-benzenebutan-2-one (1.84 g, 0.005 mol), 2,6-diisopropylphenyl isocyanate (1.15 g, 0.005 mol), and lithium diisopropylamide (0.005 mol) using the procedure described in Example 1.

EXAMPLE 20

Preparation of N-[2,6-bis(1-methylethyl)phenyl]-β-oxobenzenebutanamide

Step A: Preparation of 3-oxo-benzene-butanoic acid ethyl ester

The title compound can be prepared from phenylacetic acid by following the synthesis described in Example 3, Step A.

Step B: Preparation of 2-oxo-3-phenylpropan-2-one

The title compound was prepared from 3-oxo-benzene-butanoic acid ethyl ester (5.0 g, 0.024 mol) 1,4-diazabicyclo [2.2.2]octane (27.2 g, 0.24 mol) , and xylenes (44.4 ML, 15.0 eq) using the procedure described in Example 3, Step b.

Step C: Preparation of N-(2,6-bis(1-methylethyl)phenyl]-β-oxobenzenebutanamide The title compound was prepared from 2-oxo-3-phenyl-propan-2-one (3.0 g, 0.022 mol), 2,6-diisopropylphenyl isocyanate (4.54 g, 0.022 mol), and lithium diisopropylamide (0.022 mol) using the procedure in Example 1.

EXAMPLE 21

Preparation of N-[2,6-bis(1-methylethyl)phenyl]-β-(hydroxyimino)-δ-phenyl benzene-pentamide To a solution of N-[2,6-bis(1-methylethyl)phenyl]-β-oxo-δ-phenyl-benzene-pentanamide (1.0 g, 0.002 mol, see Example 3) in 20 mL ethanol, hydroxylamine hydrochloride (0.162 g, 0.002 mol), and sodium acetate (0.131 g, 0.0016 mol) in 2 mL H$_2$O were added (A. M. Khalil, et al, Indian J. Chem. 17B, 627 (1979)). After stirring for 1 hour at room temperature, the mixture was then concentrated in vacuo to evaporate excess ethanol. This residue was dissolved in ether, then concentrated in vacuo to afford 715.4 mg (0.0016 mol, 80.8%) of the desired product.

MS: 443 (MH+), 442 (M+).

EXAMPLE 22

Preparation of N-[2,6-bis(1-methylethyl)phenyl]-β-hydroxy-δ-phenyl-benzenelpentanamide To a cooled solution (0° C.) of sodium borohydride (0.090 g, 0.002 mol) in 20 mL ether, N-[2,6-bis(1-methylethyl)phenyl]-β-oxo-δ-phenyl-benzene pentanamide (1.0 g, 0.002 mol, see Example 3) in 20 mL THF was added dropwise. The mixture was allowed to gradually warm to room temperature and stir for 16 hours under a nitrogen atmosphere. The reaction mixture was then quenched with water and extracted with ethyl acetate. The organic layer was then washed with brine, dried (Na$_2$SO$_4$), and concentrated in vacuo to yield a crude solid. Purification by flash chromatography (silica gel, 20% EtOAc/hexane) yielded 0.34 g (0.8 mmol, 40%), MP 138°–140° C., of the desired product.

EXAMPLE 23

Preparation of β-amino-N-[2,6-bis(1-methylethyl)phenyl]-δ-phenyl-benzenepentanamide The title compound was prepared by treating N-[2,6-bis(1-methylethyl)phenyl]-β-(hydroxyimino)-δ-phenyl-benzenepentanamide (0.23 g, 0.53 mmol) with Raney nickel (0.2 g) in 50 mL methanol/ammonia at 25° C. for 18 hours (ΔP=13.7 psi). The reaction mixture was concentrated in vacuo to give a white solid, the title compound.

EXAMPLE 24

Preparation of 3-oxo-N-(2,4,6-trimethoxyphenyl)pentadecanamide

The title compound was prepared from 2-pentadecanone (0.54 g, 0.0023 mol), 2,4,6-trimethoxyphenyl isocyanate (prepared from 2,4,6-trimethoxyaniline hydrochloride and phosgene (2.5 eq)) and lithium diisopropylamide (0.0023 mol) using the procedure described in Example 1.

EXAMPLE 25

Preparation of N-[2,6-bis(1-methylethyl)phenyl]-6-(dodecylsulfonyl)-3-oxo-hexanamide

Step A: Preparation of 6-(dodecylsulfonyl)-3-oxo-hexanoic acid ethyl ester The title compound was prepared from 4-(dodecylsulfonyl)butanoic acid (H. Gilman, et al, J. Am Chem. Soc. 74, 4452 (1952)) (2.50 g, 0.07 mol), 1,1'carbonyldiimidazole (1.50 g, 0.09 mol), magnesium chloride (1.41 g, 0.014 mol), ethyl potassium malonate (2.12 g, 0.012 mol), and triethylamine (1.73 g, 0.017 mol) using the procedure described in Example 3, Step A.

Analysis for C$_{20}$H$_{38}$O$_5$S: Calcd: C, 61.50; H, 9.80; Found: C, 61.18; H, 9.76.

Step B: Preparation of 5-(dodecylsulfonyl)pentan-2-one

The title compound was prepared from 6-(dodecylsulfonyl)-3-oxo-hexanoic acid ethyl ester (2.30 g, 0.005 mol), 1,4-diazebicyclo[2.2.2]octane (6.60 g, 0.058 mol) and zylenes (10.7 ML, 15.0 eq) using the procedure described in Example 3, Step B. $^1$H NMR (ppm, CDCl$_3$): 0.85–0.90 (t, 3H), 1.17–1.43 (m, 20H), 1.76–1.88 (m, 2H), 2.03–2.14 (m, 2H), 2.16 (s, 3H) 2.96–3.03 (m, 4H),

Step C: Preparation of N-[2,6-bis(1-methylethyl)phenyl]-6-dodecylsulfonyl)-3-oxo-hexanamide The title compound was prepared from 5-dodecylsulfonyl)-pentan-2-one (1.0 g, 0.003 mol), 2,6-diisopropylphenylisocyanate (0.63 g, 0.003 mol), and lithium diisopropylamide (0.003 mol) using the procedure described in Example 1.

MS: 521.3 (M+).

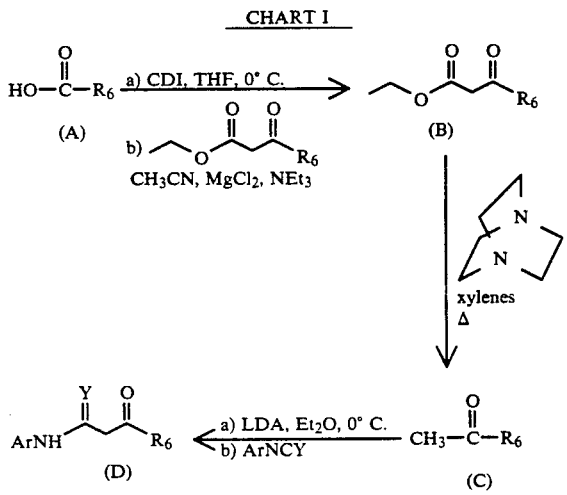

CHART I

CHART II $$(E) \xrightarrow[\text{b) Cl-C(O)-R}_6]{\text{a) LDA, THF}} (F)$$

E: ethoxy compound with Y, R_2, R_2

F: product with Y, O, R_2, R_2, R_6

$$(F) \xrightarrow[\text{5° C. → Δ}]{\text{Benzene} \mid \text{Me}_2\text{Al, ArNH}_2} (G)$$

G: ArNH-C(R_2)(R_2)-C(Y)(O)-R_6... [ArNH, R_2, Y, O, R_2, R_6]

We claim:

1. A compound of the formula $$\text{Ar}-\underset{R_1}{\underset{|}{N}}-\underset{R_2}{\underset{|}{\overset{Y}{\overset{\|}{C}}}}-\underset{R_2}{C}-Q$$

wherein Y is oxygen or sulfur;
wherein Ar is
   (a) phenyl which is substituted with from 1 to 3 substituents selected from
      methylethyl,
      trimethoxy,
      phenoxy,
      hydroxy,
      —COOH,
      —COOalkyl wherein alkyl has from 1 to 4 carbon atoms, and
      —NR$_4$R$_5$ wherein
         R$_4$ and R$_5$ are independently hydrogen or alkyl of from 1 to 4 carbon atoms;
wherein R$_1$ is hydrogen or a lower alkyl group having from 1 to 4 carbon atoms;
wherein each R$_2$ is hydrogen, a lower alkyl group having from 1 to 4 carbon atoms, or each R$_2$ taken together with the carbon atom to which it is attached forms a carbocyclic ring of from 3 to 6 carbon atoms;
wherein Q is $$-\overset{O}{\overset{\|}{C}}R_6$$

wherein R$_6$ is
   (a) phenyl which is unsubstituted or is substituted with from 1 to 3 substituents selected from
      alkyl having from 1 to 6 carbon atoms and which is straight or branched,
      alkoxy having from 1 to 6 carbon atoms and which is straight or branched,
      phenoxy,
      hydroxyl,
      fluorine,
      chlorine,
      bromine,
      nitro,
      trifluoromethyl,
      —COOH,
      —COOalkyl wherein alkyl has from 1 to 4 carbon atoms, and —NR$_4$R$_5$ wherein R$_4$ and R$_5$ are as defined above;
   (b) the group $$-(CH_2)_t-\underset{R_8}{\underset{|}{\overset{R_9}{\overset{|}{C}}}}-(CH_2)_p-R_{10}$$

wherein t is zero to 4; p is zero to 4 with the proviso that the sum of t and p is not greater than 5; R$_8$ and R$_9$ are independently selected from hydrogen or straight or branched alkyl having from 1 to 6 carbon atoms, or when R$_8$ is hydrogen, R$_9$ can be selected from the groups defined for R$_{10}$; and R$_{10}$ is phenyl or phenyl substituted with from 1 to 3 substituents selected from straight or branched alkyl having from 1 to 6 carbon atoms, straight or branched alkoxy having from 1 to 6 carbon atoms, straight or branched thioalkoxy having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or NR$_4$R$_5$ wherein R$_4$ and R$_5$ having the meanings defined above;
   (c) a straight or branched hydrocarbon chain having from 8 to 20 carbon atoms and which is saturated or contains from 1 to 3 double bonds;
   (d) the group $$-(CH_2)_q-\overset{(CH_2)_s}{\overset{|}{C}}-(CH_2)_r-Ar'$$

wherein q is zero or one to three; r is zero, one or two; s is two to six; and Ar' is phenyl or
phenyl substituted with from 1 to 3 substituents selected from
      alkyl of from 1 to 6 carbon atoms and which is straight or branched,
      alkoxy of from 1 to 6 carbon atoms and which is straight or branched,
      hydroxy,
      benzyloxy,
      fluorine,
      chlorine,
      bromine,
      nitro,
      trifluoromethyl,
      —NH—COCH$_3$,
      —CONH$_2$,
      —COOH,
      —COOalkyl wherein alkyl has from 1 to 4 carbon atoms and which is straight or branched,
      —CH$_2$COOH,
      —CH$_2$CONH$_2$, and
      —(CH$_2$)$_v$NR$_4$R$_5$ wherein v is one or two and R$_4$ and R$_5$ have the meanings defined above;
   (e) anthracene;
   (f) —(CH$_2$)$_n$—OR wherein R is hydrogen or 2-tetrahydropyran, and n is a number of from 5 to 16;

(g) 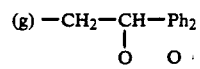

or, (h) the group 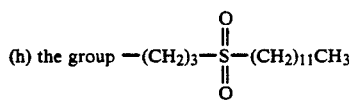

wherein R₇ is hydroxy or NH₂; or a pharmaceutically acceptable salt thereof.

2. A compound of claim 1 wherein Y is oxygen.

3. A compound of claim 1 wherein $R_1$ and $R_2$ are hydrogen.

4. A compound of claim 1 wherein $R_6$ is a straight or branched hydrocarbon chain having from 8 to 20 carbon atoms and which is saturated or contains from 1 to 3 double bonds.

5. A compound which is
3-oxo-N-(2,4,6-trimethoxyphenyl)tetradecanamide;
N,2,2-trimethyl-3-oxo-N-(2,4,6-trimethoxy-phenyl)-tetradecanamide;
2,2-dimethyl-3-oxo-N-(2,4,6-trimethoxy-phenyl)-tetradecanamide; or
3-oxo-N-(2,4,6-trimethoxyphenyl)pentadecanamide.

6. A compound which is
N-[2,6-bis(1-methylethyl)phenyl]-3-oxo-tetradecanamide;
N,2,2-trimethyl-3-oxo-N-[2,6-bis(1-methylethyl)-phenyl]tetradecanamide;
N-[2,6-bis(1-methylethyl)phenyl]-3-oxopentadecanamide;
N-[2,6-bis(1-methylethyl)phenyl]-3-oxohexadecanamide;
N-[2,6-bis(1-methylethyl)phenyl]-3-oxododecanamide;
N-[2,6-bis(1-methylethyl)phenyl]-3-oxotridecanamide; or
N-[2,6-bis(1-methylethyl)phenyl]-3-oxoheptadecanamide.

7. A compound of claim 1 wherein $R_6$ is the group:

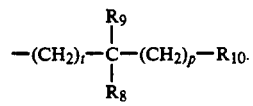

8. A compound which is
N-[2,6-bis(1-methylethyl)phenyl]-β-oxo-phenylbenzenebutanamide;
N-[2,6-bis(1-methylethyl)phenyl]-β-oxo-δ-phenylbenzenepentanamide; or
N-[2,6-bis(1-methylethyl)phenyl]-β-oxobenzenebutanamide.

9. A compound which is
N-[2,6-bis(1-methylethyl)phenyl]-β-oxobenzenepropanamide.

10. A compound which is
N-[2,6-bis(1-methylethylphenyl]-β-oxo-1-phenylcyclopentanepropanamide; or
N-[2,6-bis(1-methylethyl)phenyl]-6-(dodecylsulfonyl)-3-oxo-hexanamide.

* * * * *

UNITED STATES PATENT AND TRADEMARK OFFICE
CERTIFICATE OF CORRECTION

PATENT NO. : 5,278,326
DATED : January 11, 1994
INVENTOR(S) : Corinne E. Augelli, et al.

It is certified that error appears in the above-identified patent and that said Letters Patent is hereby corrected as shown below:

Column 19, line 62, "hydroxyl" should read "hydroxy".

Column 20, lines 35-39, " $-(CH_2)_q-C-(CH_2)_r-Ar$ "

$(CH_2)_s$ should read " $-(CH_2)_q-C-(CH_2)_r-Ar$ "

$\underset{(CH_2)_s}{\overset{}{\bigcirc}}$

.

UNITED STATES PATENT AND TRADEMARK OFFICE
CERTIFICATE OF CORRECTION

PATENT NO. : 5,278,326
DATED : January 11, 1994
INVENTOR(S) : Corinne E. Augelli-Szafran, et al.

It is certified that error appears in the above-indentified patent and that said Letters Patent is hereby corrected as shown below:

Column 21, lines 3-4, " 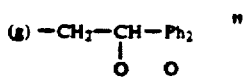 "

should read "  "

Signed and Sealed this

Seventh Day of June, 1994

Attest:

BRUCE LEHMAN

*Attesting Officer*   Commissioner of Patents and Trademarks